(12) United States Patent
Savage

(10) Patent No.: US 7,306,928 B2
(45) Date of Patent: *Dec. 11, 2007

(54) HOMOGENOUS ASSAY FOR ENZYMATIC ACTIVITY

(75) Inventor: M. D. Savage, Conroe, TX (US)

(73) Assignee: Pierce Biotechnology, Inc., Rockford, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/517,758

(22) PCT Filed: Jun. 16, 2003

(86) PCT No.: PCT/US03/18912

§ 371 (c)(1),
(2), (4) Date: Oct. 14, 2005

(87) PCT Pub. No.: WO03/106703

PCT Pub. Date: Dec. 24, 2003

(65) Prior Publication Data

US 2006/0148024 A1  Jul. 6, 2006

Related U.S. Application Data

(60) Provisional application No. 60/388,792, filed on Jun. 14, 2002.

(51) Int. Cl.
*G01N 33/53* (2006.01)
*C12Q 1/48* (2006.01)
*C12Q 1/42* (2006.01)
*C12Q 1/37* (2006.01)

(52) U.S. Cl. .................. 435/7.72; 435/15; 435/21; 435/23

(58) Field of Classification Search .................. None
See application file for complete search history.

(56) References Cited

U.S. PATENT DOCUMENTS 5,034,189 A * 7/1991 Cox et al. .................. 422/52
6,472,141 B2 * 10/2002 Nikiforov .................. 435/4
6,689,565 B2 * 2/2004 Nikiforov .................. 435/6
6,699,655 B2 * 3/2004 Nikiforov .................. 435/4

FOREIGN PATENT DOCUMENTS

WO   WO-00/72016 A1   11/2000
WO   WO-01/07638 A2   2/2001

OTHER PUBLICATIONS

International Search Report (3 pages), 2003.

* cited by examiner

*Primary Examiner*—Jon Weber
*Assistant Examiner*—Paul Martin
(74) *Attorney, Agent, or Firm*—Thompson Hine LLP

(57) ABSTRACT

An assay is disclosed for measuring activity of enzymes, such as kinases, phosphatases, and proteases. Measurements of enzymatic activity are accomplished in a homogenous assay format utilizing a fluorescence quenching technique employing paramagnetic metal ions.

5 Claims, 16 Drawing Sheets

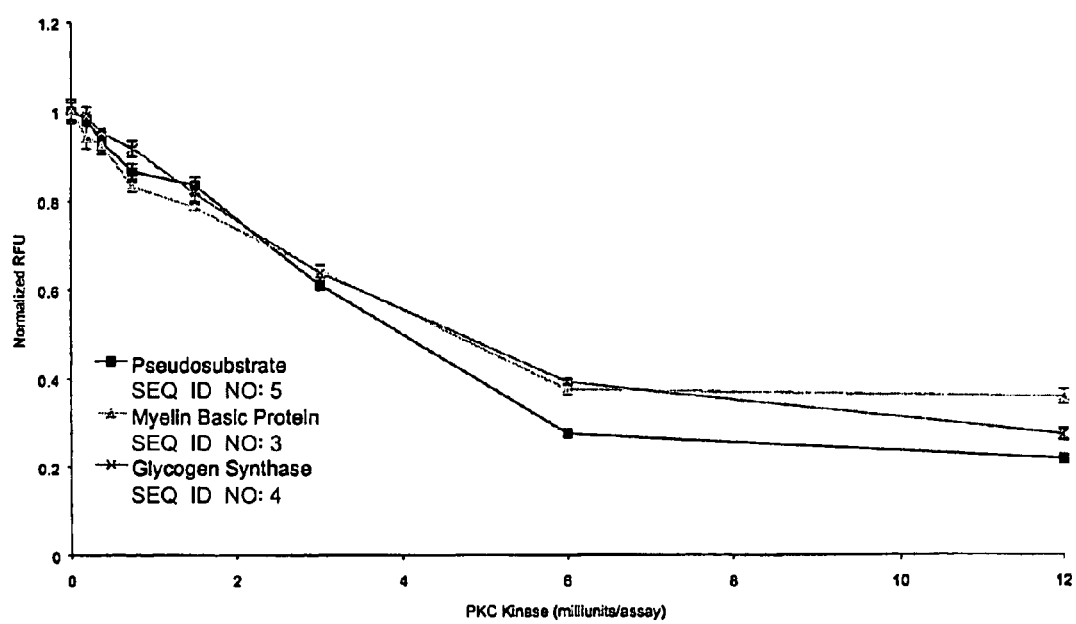
Fig 1. PKC detection in a black 384 well plate.

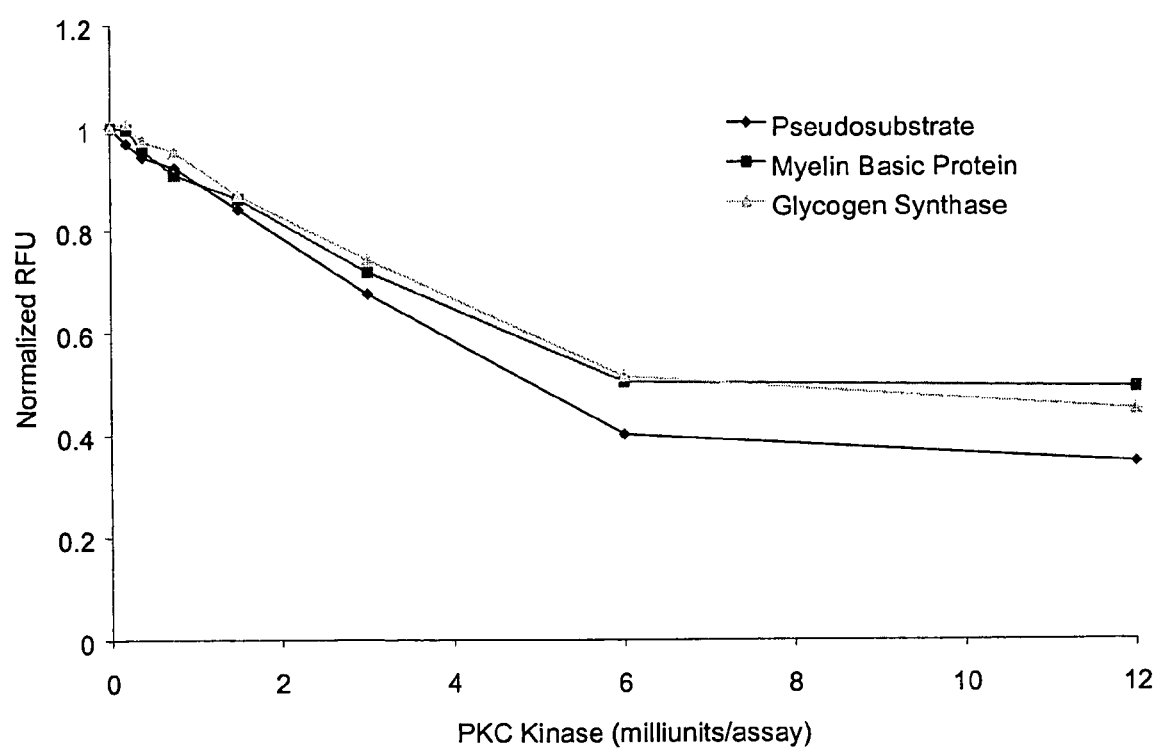
Fig 2. PKC detection in a white 384 well plate.

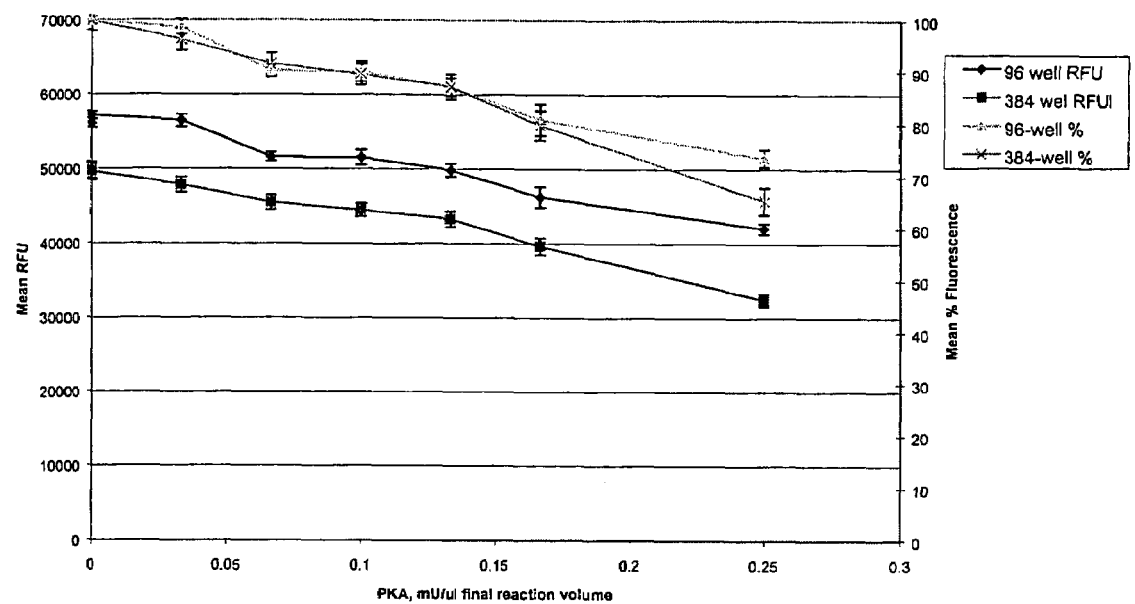
Fig 3. PKA Detection in 96 and 384 white plates.

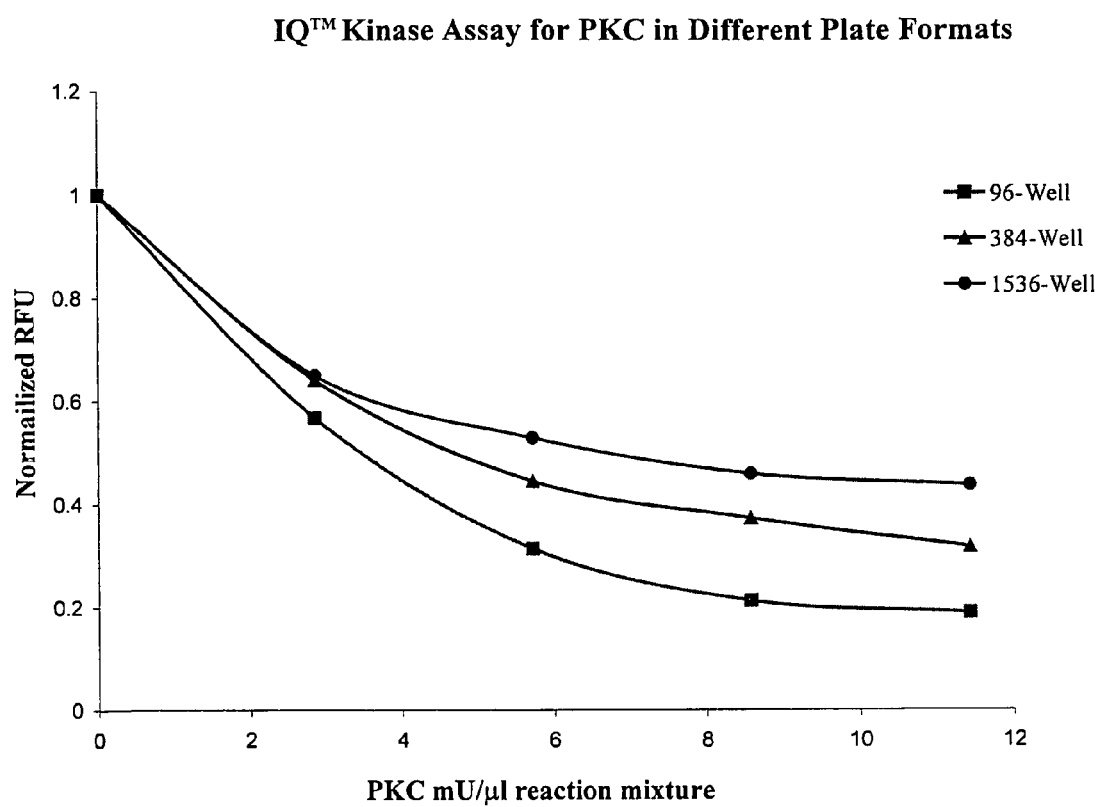
Fig 4. PKC detection comparison in various plate density formats using Pseudosubstrate peptide

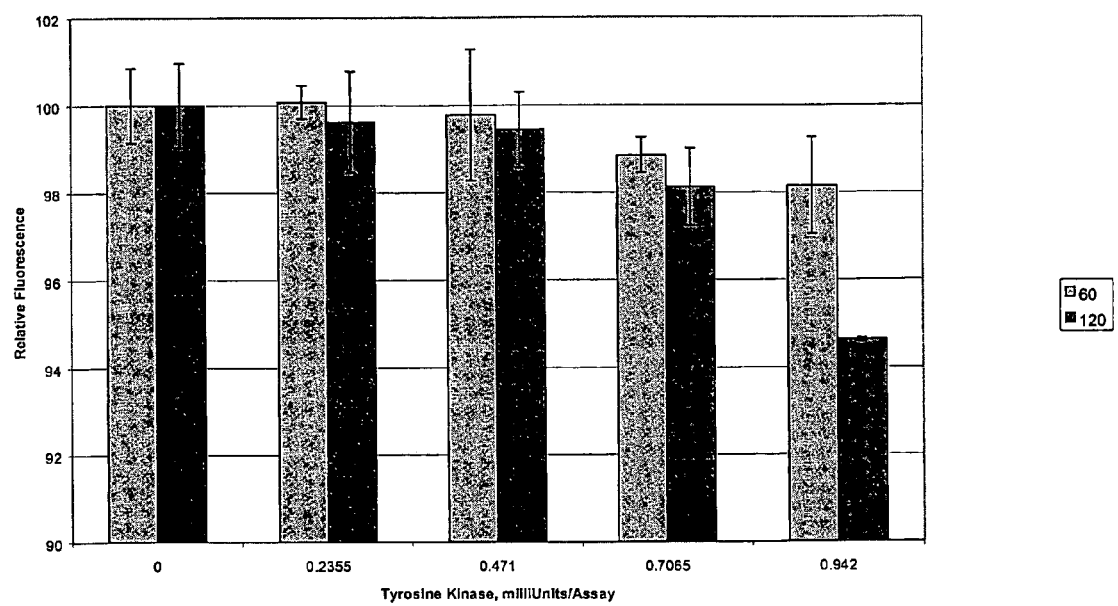
Fig 5. Tyrosine Kinase time course detection after 60 or 120 minutes of enzyme reaction.

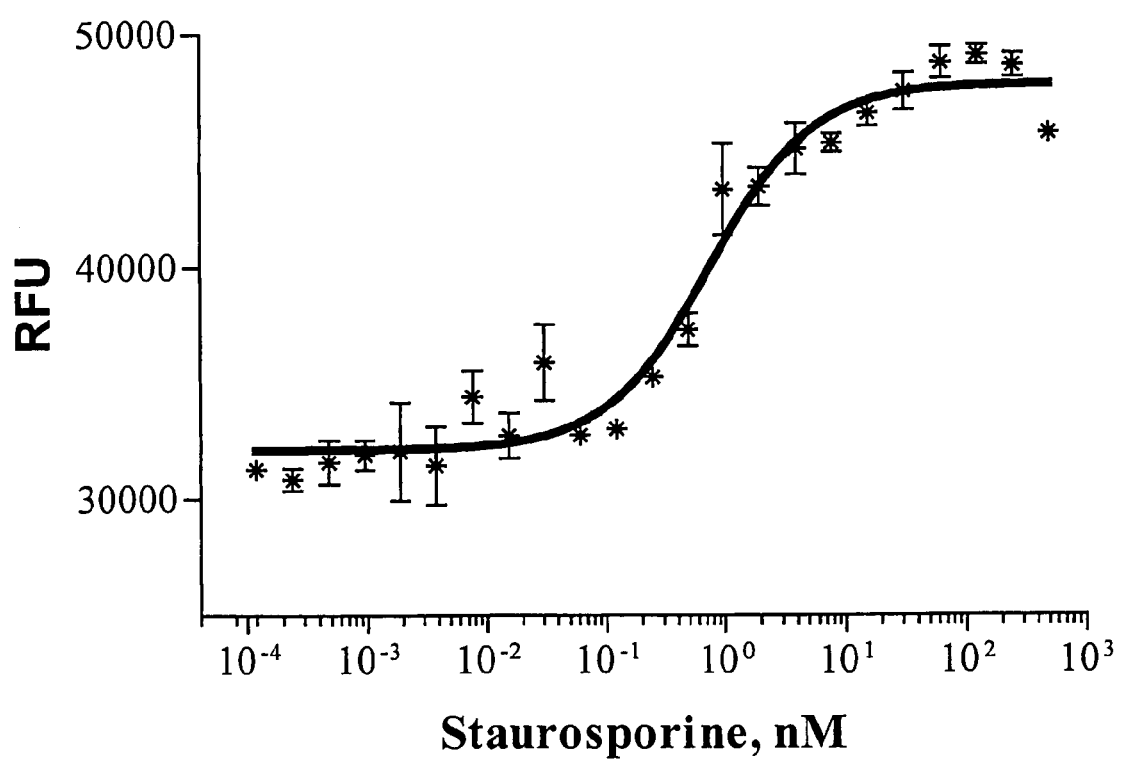
Fig 6. Assay of staurosporine inhibition on PKC activity.

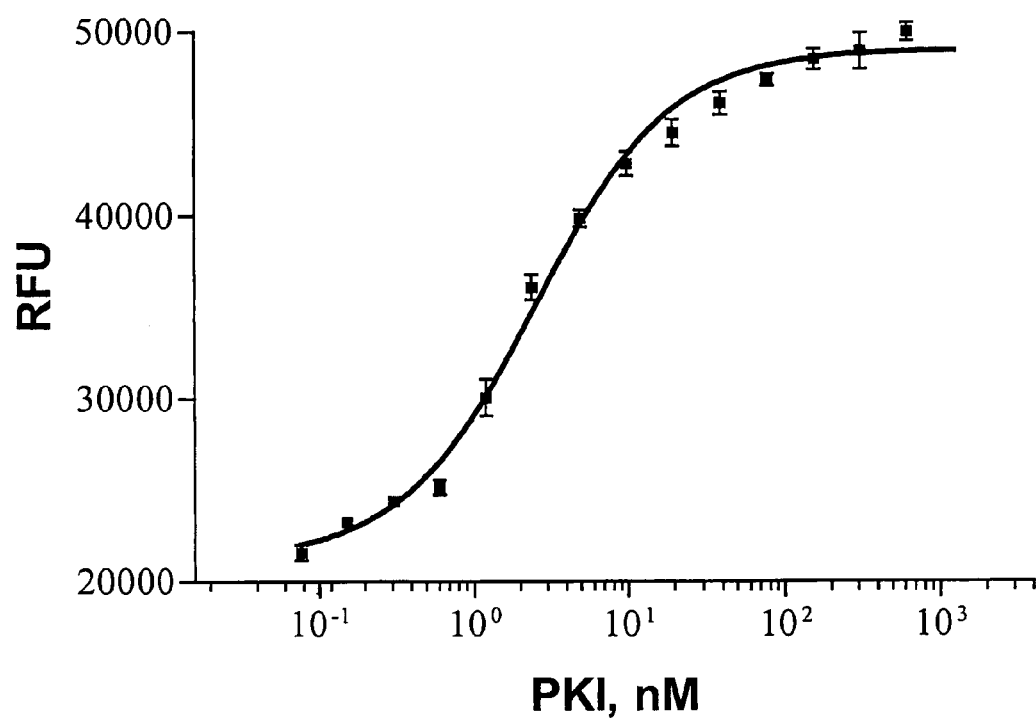
Fig 7. Assay of PKI inhibition on PKA activity

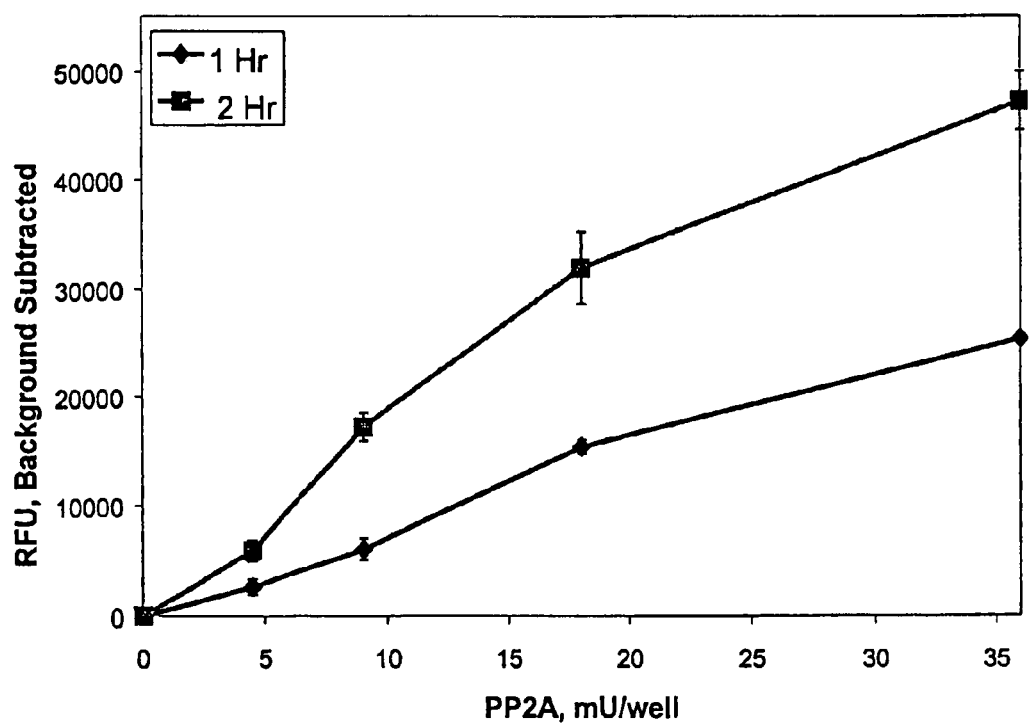
Fig. 8. PP2A Phosphatase activity was measured in the presence of the peptide substrate, SEQ ID NO: 1. Several concentrations of enzyme and two timepoints were analyzed.

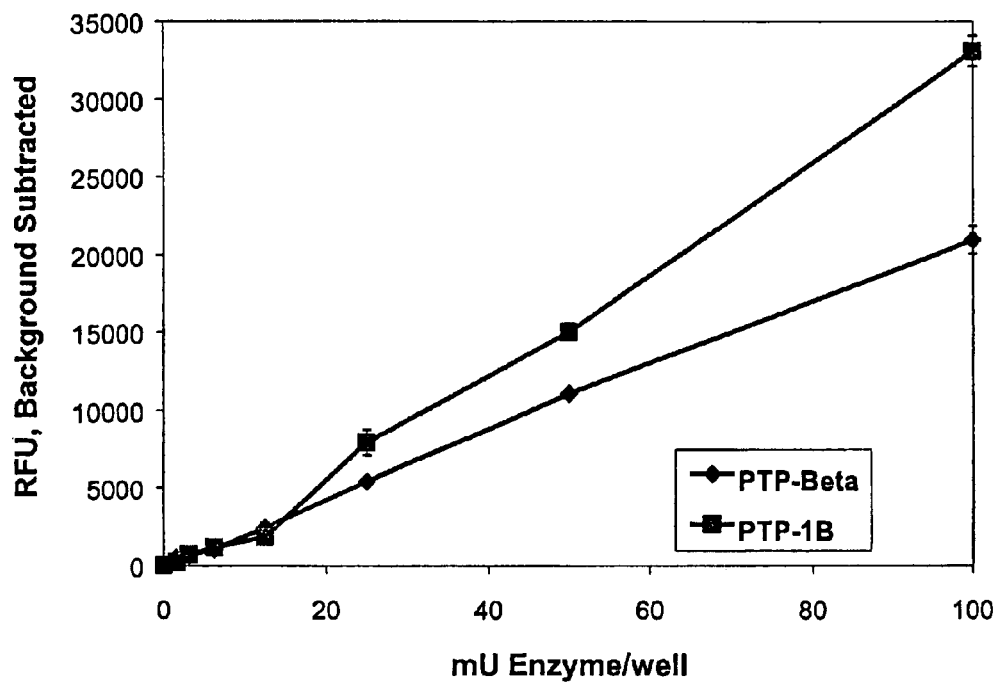
Fig. 9. PTP-Beta or PTP1B Phosphatase activity was measured in the presence of the peptide substrate, SEQ ID NO: 8. Several concentrations of enzyme were analyzed.

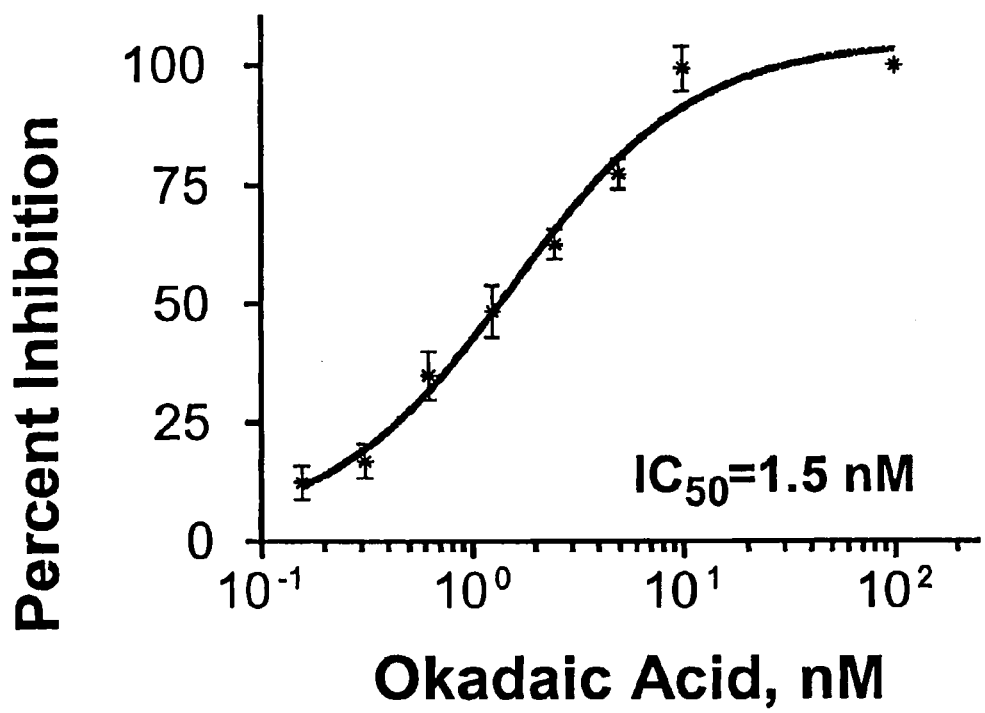
Fig. 10. Assay of Okadaic Acid inhibition on PP2A Phosphatase activity using Lissamine Rhodamine labeled phosphopeptide substrate, SEQ ID NO: 1.

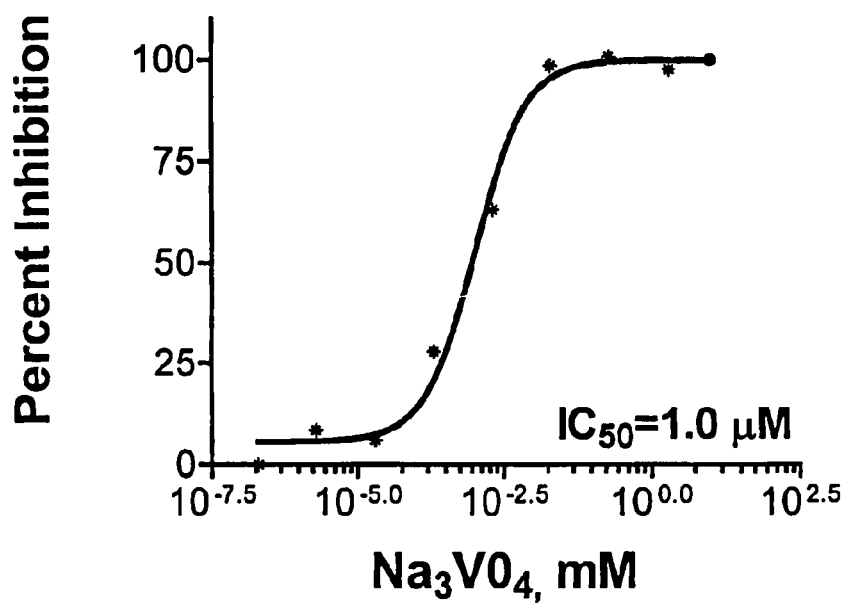
Fig. 11. Assay of sodium ortho-vanadate inhibition on PTP1B Phosphatase activity using Lissamine Rhodamine labeled phosphopeptide substrate SEQ ID NO: 8.

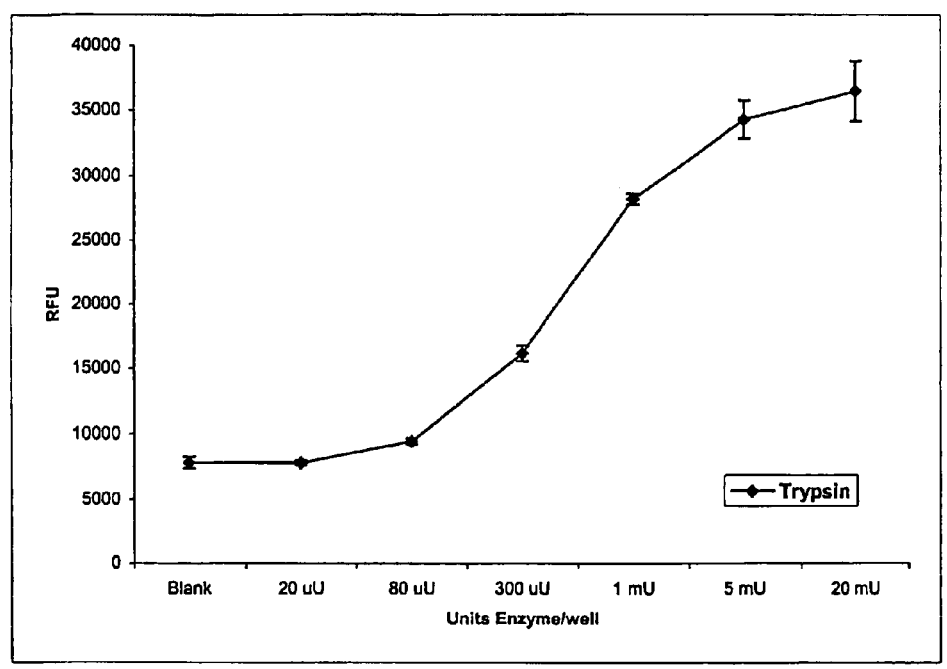
Fig. 12 Trypsin activity assay using Lissamine rhodamine labeled SEQ ID NO: 1 as the enzymatic substrate.

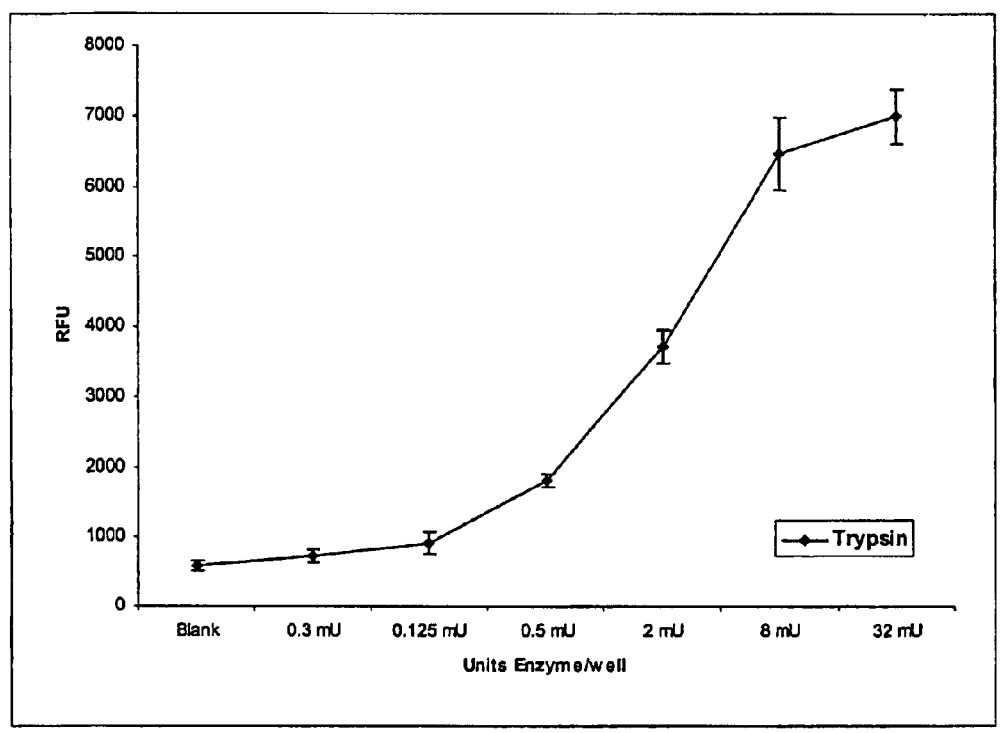
Fig 13 Trypsin activity assay using Lissamine rhodamine labeled SEQ ID NO: 2 as the enzymatic substrate.

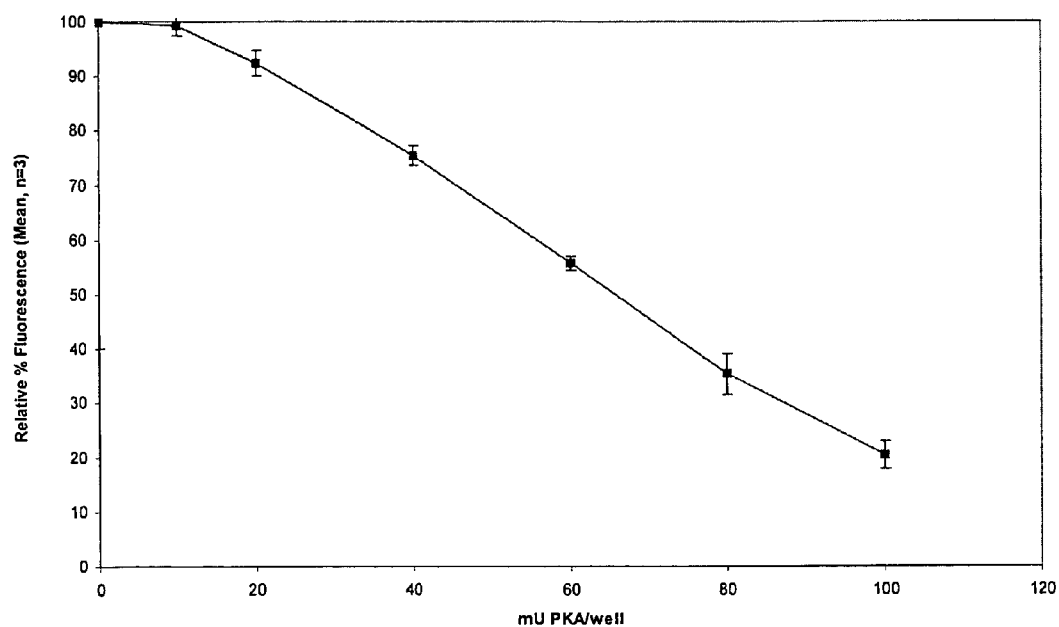
Fig. 14 PKA activity assay using fluorescein labeled Kemptide substrates

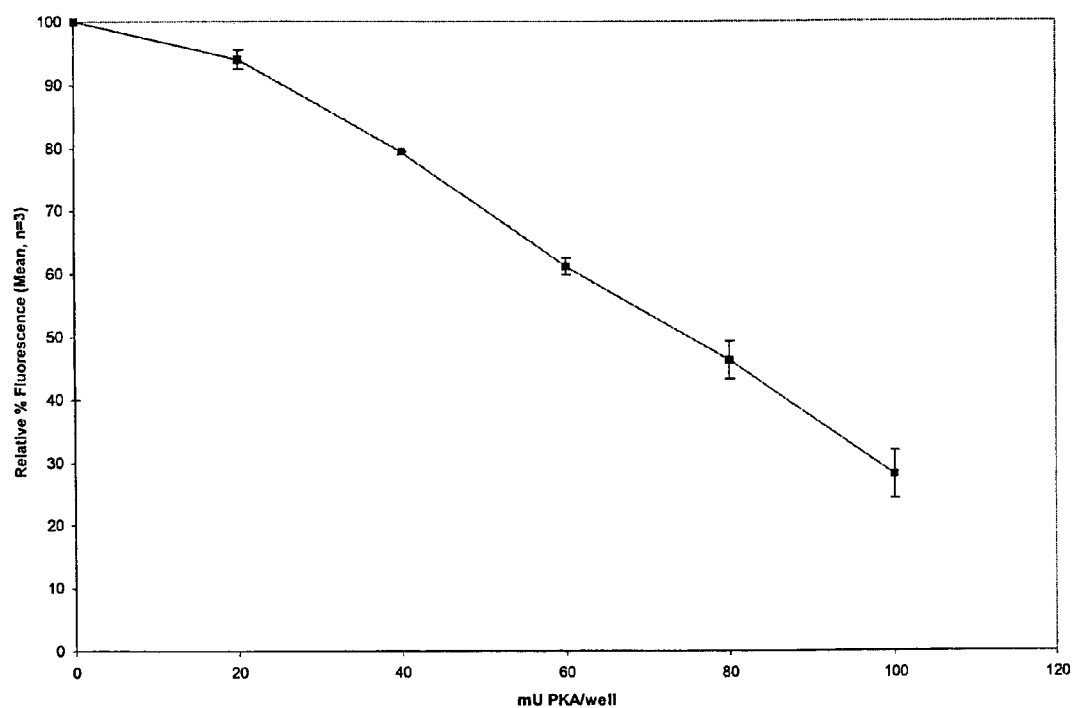
Fig. 15. PKA activity assay using Oregon Green labeled Kemptide substrates

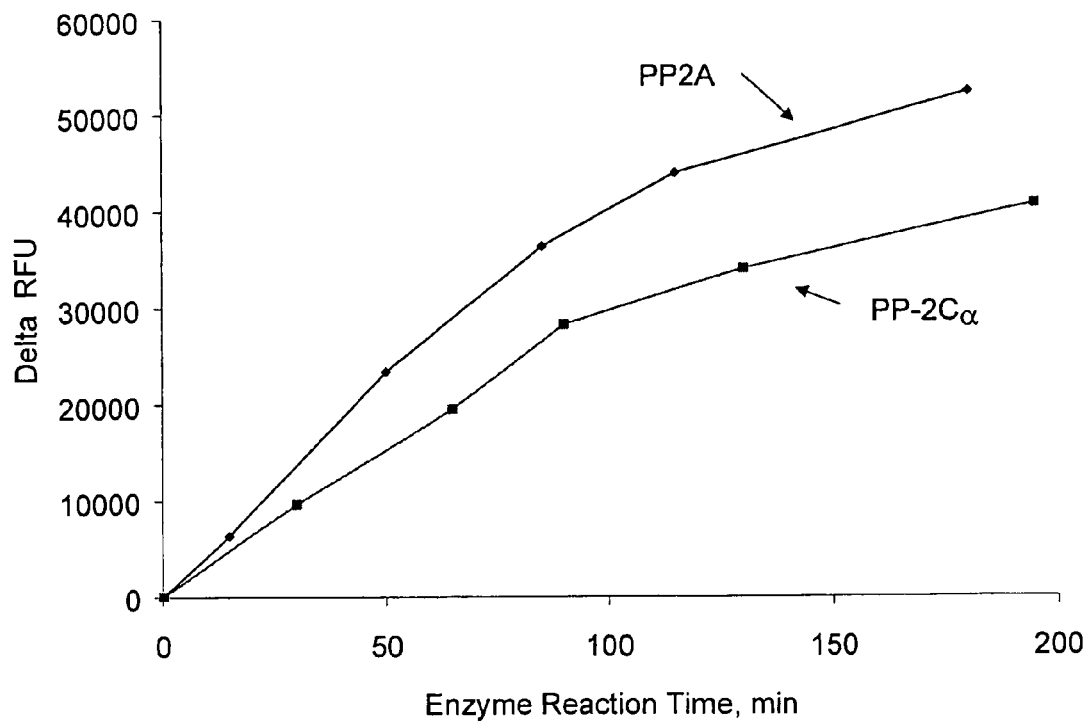
Fig. 16 Assay for protein phosphastase activity using either phosphatases PP-2Cα or PP2 with Lissamine Rhodamine labeled phosphoKemptide substrate.

SEQUENCE LISTING

<160> NUMBER OF SEQ ID NOS: 8

<210> SEQ ID NO 1
<211> LENGTH: 7
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: PHOSPHORYLATION

<400> SEQUENCE: 1

Leu Arg Arg Ala Ser Leu Gly
1               5

<210> SEQ ID NO 2
<211> LENGTH: 22
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (21)..(21)
<223> OTHER INFORMATION: PHOSPHORYLATION

<400> SEQUENCE: 2

Ala Gly Leu Ala Arg Ala Gly Leu Ala Leu Ala Arg Leu Ala Leu Ala
1               5                   10                  15

Leu Arg Arg Ala Ser Leu
            20

<210> SEQ ID NO 3
<211> LENGTH: 11
<212> TYPE: PRT
<213> ORGANISM: Artificial
<220> FEATURE:
<223> OTHER INFORMATION: Synthetic Construct

<400> SEQUENCE: 3

Glu Lys Arg Pro Ser Gln Arg Ser Lys Tyr Leu
1               5                   10

<210> SEQ ID NO 4
<211> LENGTH: 12
<212> TYPE: PRT
<213> ORGANISM: Artificial
<220> FEATURE:
<223> OTHER INFORMATION: Synthetic Construct

<400> SEQUENCE: 4

Pro Leu Ser Arg Thr Leu Ser Val Ala Ala Lys Lys
1               5                   10

<210> SEQ ID NO 5
<211> LENGTH: 13
<212> TYPE: PRT
<213> ORGANISM: Artificial
<220> FEATURE:
<223> OTHER INFORMATION: Synthetic Construct

<400> SEQUENCE: 5

Arg Phe Ala Arg Lys Gly Ser Leu Arg Gln Lys Asn Val
1               5                   10

```
<210> SEQ ID NO 6
<211> LENGTH: 7
<212> TYPE: PRT
<213> ORGANISM: Artificial
<220> FEATURE:
<223> OTHER INFORMATION: Synthetic Construct

<400> SEQUENCE: 6

Leu Arg Arg Ala Ser Leu Gly
1               5

<210> SEQ ID NO 7
<211> LENGTH: 15
<212> TYPE: PRT
<213> ORGANISM: Artificial
<220> FEATURE:
<223> OTHER INFORMATION: Synthetic Construct

<400> SEQUENCE: 7

Lys Val Glu Lys Ile Gly Glu Gly Thr Tyr Gly Val Val Tyr Lys
1               5                   10                  15

<210> SEQ ID NO 8
<211> LENGTH: 15
<212> TYPE: PRT
<213> ORGANISM: Artificial
<220> FEATURE:
<223> OTHER INFORMATION: Synthetic Construct
<220> FEATURE:
<221> NAME/KEY: MOD_RES
<222> LOCATION: (10)..(10)
<223> OTHER INFORMATION: PHOSPHORYLATION

<400> SEQUENCE: 8

Lys Val Glu Lys Ile Gly Glu Gly Thr Tyr Gly Val Val Tyr Lys
1               5                   10                  15
```

HOMOGENOUS ASSAY FOR ENZYMATIC ACTIVITY

FIELD OF INVENTION

The present invention relates to the assay of enzymatic activity and, more particularly, to the measurement of the activity of kinases, phosphatases, and proteases, as well as other enzymes. More specifically, the present invention relates to measurements of enzymatic activity, which are accomplished in a homogenous assay format utilizing a fluorescence quenching technique employing paramagnetic metal ions.

BACKGROUND OF INVENTION

Enzymes are catalytic proteins that typically act on a substrate to yield an endproduct. Protein kinases and protein phosphatases comprise a class of enzymes that modify protein and/or peptide substrates by catalyzing the attachment or removal, respectively, of a phosphoryl group to sites on certain amino acid side chains of the substrates for these enzymes. Determining the presence or catalytic activity of these enzymes is important since the degree of phosphorylation of a particular protein or peptide has been found to be an important characteristic in regulating cellular functions. Enzymes capable of peptide bond cleavage, known as proteases, are another class of enzymes. Ever increasing emphasis is being placed on discovering what drugs can be used to modulate enzyme activity. This, in turn, has created the demand for the development of improved techniques for the measurement of the activity of enzymes.

Radioactive detection has been used to assay for enzymatic activity; see, for example, U.S. Pat. No. 5,538,858. With respect to kinases, a sample containing the kinase of interest is incubated with activators and a peptide substrate in the presence of radioactive labeled ATP. Then, an aliquot of the incubated mixture (containing phosphorylated and non-phosphorylated peptides) is placed on a filter that binds the substrate and the filter washed to remove excess radioactivity. The amount of radiolabeled phosphate incorporated into the substrate and, in turn, enzyme activity is measured by scintillation counting.

Because of the necessity for the precautions involved in radioactive techniques, non-radioactive assay techniques are also in use. A particularly attractive assay is sold by Pierce Biotechnology, Inc. (formerly known as Pierce Chemical Company) under the SpinZyme™ brand name and is described in U.S. Pat. No. 5,527,688, issued on Jun. 18, 1996. In this assay, non-radioactive ATP is used in the incubation mixture and the substrate is dye-labeled. After the enzymatic reaction, the incubated mixture is brought into contact with a solid phase containing immobilized $Fe^{+++}$. The phosphorylated substrate in the mixture binds to the solid phase by chelation with the iron ion. The non-phosphorylated substrate is removed by washing, and the amount of phosphorylated substrate is measured by detection of the dye, which is labeled on the substrate.

The above-described assay techniques are non-homogenous in that they require the phosphorylated and non-phosphorylated substrates to be physically separated between the kinase-initiated phosphorylation and detection. These added steps detract from the use of these techniques in those applications commonly used in drug screening and termed high throughput screening.

Homogenous assay techniques have been developed in a variety of specific areas to overcome the aforementioned drawbacks of non-homogenous assays. One example is radioactive assays, commonly known as scintillation proximity assays. These are described in U.S. Pat. Nos. 4,568,649, 5,665,562 and 5,989,854. Other homogenous assays are described in the April, 2002 issue of Drug Discovery & Development entitled "The Key to Kinases is All in the Kits," beginning on page 28.

Several other categories of homogenous assays are based on non-radioactive detection methods. Fluorescence techniques, such as based on fluorescence resonance energy transfer (FRET) and fluorescence polarization (FP), have been introduced; see, for example, U.S. Pat. No. 6,287,774 and US Patent Application 2002/0034766 A1.

In FRET methods, a fluorophore (a light-absorbing dye capable of fluorescence emission) is utilized in combination with another fluorophore (either identical or not) or with a chromophore (a light-absorbing dye not capable of fluorescence emission). A general requirement for FRET is that the two entities of the pair combination (either fluorophore and fluorophore, or fluorophore and chromophore) have an overlapping spectral region. The ability of the FRET technique to be utilized in the construction of an assay relies on the capacity to distinguish, by measurable signal detection, the variation in observed fluorescent emission from the combination pairs employed when they are in close proximity as opposed to spatially separated. Thus, in this technique, a donor fluorophore, such as fluorescein, can be used with the dye, tetramethylrhodamine, as an acceptor fluorophore. When these two fluorophores are in close proximity to each other, excitation of the fluorescein molecule results in energy being transferred to the tetramethylrhodamine acceptor and consequently the normal expected emission from the fluorescein is decreased.

Assays can be constructed using FRET techniques where specific binding events are utilized to bring the two fluorophores into close proximity. Such assays can be quantitated by observing decreased fluorescent emission of the donor fluorophore or by observing increased fluorescent emission of the acceptor fluorophore, both of which are brought about when the binding event occurs. Proteolytic FRET assays utilize the action of a protease to cleave the substrate having the attached fluorophores (for example labeled on the N and C terminus of peptide) to cause the two fluorophores to be more spatially separated and thereby diminishing the FRET event.

In the case of FRET assays utilizing a chromophore, examples of useful chromophores include those commonly known as Black Hole Quenchers and DABCYL (4-(4'-dimethylaminophenylazo)benzoic acid) (See Proc. Natl. Acad. Sci. USA. 1999 May 25; 96 (11): 6394-6399 entitled "Multiplex detection of four pathogenic retroviruses using molecular beacons." Jacqueline A. M. Vet, Arnit R. Majithia, Salvatore A. E. Marras, Sanjay Tyagi, Syamalima Dube, Bernard J. Poiesz, and Fred Russell Kramer).

Drawbacks of the FRET technique include the requirement of a matched combination pair, which precludes a more universal utility to assay construction, along with other drawbacks, such as increased cost, complications related to assay interpretation via signal breakthrough, and negative assay interactions, such as hydrophobic interactions of the enzyme with the dye molecules, etc.

Turning now to the FP method mentioned above, this technique relies on detecting a measurable change in fluorescent polarization. For example, in FP-based kinase assay, these assays measure the change in fluorescent polarization (FP) that accompanies the kinase catalyzed phosphorylation of a fluorescent dye-labeled substrate. To achieve a measurable change in FP on phosphorylation, a large entity is included in the incubation mixture, which complexes with the phosphoryl group on the derivatized peptides. In such a direct assay format, because of the resulting increase in size of those peptides that have been phosphorylated, their rotational diffusion is significantly less and, in turn, their FP significantly greater, than of those peptides that have not been phosphorylated. Competitive FP formats also have been described. Thus, the difference in FP between the labeled substrate before catalysis with the kinase of interest and after catalysis is indicative of the activity of the enzyme.

FP assays can be run in a homogenous format, which requires no washing and separation steps because both the before and after measurements are of the same parameter, namely, fluorescent polarization; only the change in this parameter is the determinative factor. However, a drawback associated with FP assays is the necessity for using expensive equipment capable of measuring FP. A further drawback of FP assays resides in certain technical limitations associated with its use, such as assay artifacts due to scattered light, viscosity changes, and polarization changes associated with incorporation of small molecular weight fluorophores into large molecular detergent micelles. These limitations are not found in fluorescent assays based on simple measurement of fluorescent intensity.

SUMMARY OF INVENTION

In accordance with the present invention there is provided a method and associated composition of matter for assaying the activity of an enzyme based on fluorescence quenching. The present invention results from the observation that the fluorescent intensity of a fluorophore label on an enzymatic substrate or endproduct can be quenched by the presence of a paramagnetic metal ion when bound to a target group located in proximity to the label, and the realization that useful enzyme assays are enabled utilizing this observation.

The assays incorporate a paramagnetic multivalent ion that binds specifically to a target group present on a fluorescent dye-labeled enzymatic substrate or endproduct. When bound to the target group, the ion is brought into proximity to the fluorophore and acts as a quencher of the fluorescent dye label by means of intrinsic properties of the metal ion. This specific binding is immediate. Results are quantitated by comparing the observed relative fluorescence units of test samples to blanks containing no enzyme.

More specifically, the method of the present invention involves assaying the activity of an enzyme of choice by contacting the enzyme with a population of fluorophore labeled substrate in an aqueous enzymatic reaction mixture, and allowing the enzymatic reaction to proceed for a selected period of time and temperature as desired. The reaction is then brought into contact with a paramagnetic metal ion to form a complex of the paramagnetic metal ion with a target group on either the enzyme substrate or endproduct. This complex, when in proximity to the fluorophore label, causes specific quenching of the fluorescence from the fluorophore. By measuring the intensity of the observed fluorescent emission from the mixture and relating the observed fluorescence to that of an external reference, a differential fluorescent signal, if any, can be identified and quantitated to ascribe a specific value to the differential. This ascribed differential value in fluorescent signal of the sample is indicative of the final state (i.e., post-enzymatic reaction) of the fluorophore labeled substrate population and, in turn, reflects enzymatic activity.

Assays using the present invention can be practiced in several formats. In one embodiment the enzyme is reacted with a substrate to produce an endproduct containing a target group having binding affinity for the paramagnetic metal ion. In another embodiment, the enzyme reaction removes such target group from the substrate. In both instances, the substrate contains an attached fluorophore label.

The method of this invention is particularly applicable in the assay of kinase and phosphatase activity, including kinases and phosphatase acting upon peptide substrates. In both of these cases the target group is a phosphoryl group. The endproduct is the fluorophore labeled substrate, which has either been phosphorylated in the case of kinase or dephosphorylated in the case of phosphatase. In the kinase assay, after addition of the paramagnetic metal ion to the endproduct, enzyme activity is evidenced by decreased fluorescent intensity with increasing enzymatic activity. The decrease in fluorescent intensity arises as a consequence of the increased content of peptide moieties containing phosphoryl groups in the overall population of fluorophore labeled peptide present in the final enzyme reaction mixture.

With respect to phosphatase enzyme assays, by virtue of the fluorophore labeled substrate being already phosphorylated, the initial starting enzymatic reaction will be more highly quenched prior to the enzymatic reaction. Thus, the observed fluorescent emission from the population after enzymatic removal of phosphoryl groups will be observed to increase with increasing phosphatase activity since the action of the enzyme will result in a decrease in the overall population of fluorophore labeled peptides containing the attached phosphoryl groups.

As can be seen from the two prior cases, the actual assay can result in either a decrease or increase in fluorescence. It should be noted, however, that, in both cases, the mechanism relies on a specific quenching caused by paramagnetic metal ion with its target group.

Protease activity also can be assayed by the method of the present invention. In this case, a protease substrate is selected to have a proteolytic cleavage site between the attached fluorophore on the substrate and a target group, which can be an imidazole or phosphoryl group. As such the target group resides in proximity to the label and, upon binding, the paramagnetic metal to the target group, the metal ion is consequently brought into proximity to the fluorophore label. As with the case of the above mentioned phosphatase assays, the protease assay will be observed to exhibit an increase in observed fluorescent emission with an increase in protease activity. This is because the protease will cleave the substrate to result in a population having fluorophore labels with increased spatial separation as compared to the initial substrate where the label is in close proximity to the paramagnetic metal ion/target group complex.

Another aspect of the present invention resides in providing a composition which is formed in the fluorescence quench-based homogenous assays for enzymatic activity described above. This composition comprises a paramagnetic metal ion and a substrate for an enzyme or an enzymatic endproduct resulting from reaction of the enzyme with a substrate. The substrate or endproduct contains a fluorophore label and also contains a target group to which the paramagnetic metal ion is bound, thus permitting the formation a complex of the target and ion. The complex is in proximity to the fluorophore and causes specific quenching of the fluorescence of the label when the complex forms.

Yet a further embodiment of this invention provides a kit comprised of a paramagnetic metal ion and an instruction booklet referencing and/or describing the manner in which the assay can be accomplished with respect to one or more enzymes as set forth herein. The kit may include a synthetically prepared calibrator to function as an external reference. The calibrator includes a fluorophore labeled synthetic compound having one or more concentrations of the attached target group of interest, each in separate packages.

BRIEF DESCRIPTION OF THE DRAWINGS

FIG. 1 shows the assay for PKC enzyme activity using three different enzymatic substrates labeled with Lissamine rhodamine and conducted in a 384 well format using an opaque black plate. The data represent the means of triplicates and error bars show the standard deviation. The observed fluorescent signal decreases with increasing amounts of enzymatic activity.

FIG. 2 shows the assay for PKC enzyme activity using three different enzymatic substrates labeled with Lissamine rhodamine and conducted in a 384 well format using an opaque white plate. The data represent the means of triplicates and error bars show the standard deviation. The observed fluorescent signal decreases with increasing amounts of enzymatic activity.

FIG. 3 shows the assay for PKA enzyme using Lissamine rhodamine labeled Kemptide and conducted in either a 96 or 384 well format using opaque white plates. The data represent the means of triplicates and error bars show the standard deviation. The observed fluorescent signal decreases with increasing amounts of enzymatic activity. The graph illustrates the raw observed signal as mean RFU or as the normalized signal expressed as the mean percentage of RFU relative to the zero enzyme point assigned to 100% fluorescence.

FIG. 4 shows the assay for PKC enzymatic activity using Lissamine rhodamine labeled pseudosubstrate activity conducted in either a 96, 384 or 1536 well formats using opaque white plates. The graph illustrates the normalized fluorescent signal expressed relative to the zero enzyme point assigned a relative value of 1.0.

FIG. 5 shows the assay for tyrosine kinase activity using Lissamine rhodamine labeled TK1 peptide where the enzyme was allowed to react for either one or two hours in a 96 well opaque white plate. The data represent the means of triplicates and error bars show the standard deviation. The observed fluorescent signal decreases with increasing amounts of enzymatic activity. The observed fluorescent signal is more highly quenched at each enzyme concentration with two hours of enzymatic reaction as compared to one hour of enzymatic reaction time, confirming the time-dependency of the enzymatic reaction.

FIG. 6 shows the inhibition of PKC activity by staurosporine. The observed fluorescent signal is differentially quenched relative to the amount of inhibitor supplied to the enzyme reaction mixture. The degree of observed fluorescent correlates to the amount of enzymatic activity. The enzymatic activity is higher at lower concentrations of inhibitor, and therefore the observed RFU is decreased.

FIG. 7 shows the inhibition of PKA activity by PKI. The observed fluorescent signal is differentially quenched relative to the amount of inhibitor supplied to the enzyme reaction mixture. The degree of observed fluorescent correlates to the amount of enzymatic activity. The enzymatic activity is higher at lower concentrations of inhibitor, and therefore the observed RFU is decreased.

FIG. 8 shows the assay for PP2A phosphatase activity using Lissamine rhodamine labeled peptide substrate SEQ ID NO: 1 at one or two hours of enzymatic reaction in a 96 well plate format. The data represent the means of triplicates and error bars show the standard deviation. The observed fluorescent signal increases with increasing amounts of enzymatic activity. The observed fluorescent signal is less quenched at each enzyme concentration with two hours of enzymatic reaction as compared to one hour of enzymatic reaction time, confirming the time-dependency of the enzymatic reaction.

FIG. 9 shows the assay for PTPB or PTP1B phosphatase activity using Lissamine rhodamine labeled peptide substrate using the phosphorylated TK1 peptide in a 96 well plate format. The data represent the means of triplicates and error bars show the standard deviation. The observed fluorescent signal increases with increasing amounts of enzymatic activity.

FIG. 10 shows the assay for inhibition of PP2A activity by okadaic acid. The observed fluorescent signal is differentially quenched relative to the amount of inhibitor supplied to the enzyme reaction mixture. The data are normalized by assigning the observed RFU to equal 100% enzyme inhibition at the highest concentration of inhibitor tested.

FIG. 11 shows the assay for inhibition of PTP1B activity by sodium ortho-vanadate. The observed fluorescent signal is differentially quenched relative to the amount of inhibitor supplied to the enzyme reaction mixture. The data are normalized by assigning the observed RFU to equal 100% enzyme inhibition at the highest concentration of inhibitor tested.

FIGS. 12 and 13 shows the assay for proteolytic enzymatic activity of TPCK-treated trypsin using the Lissamine labeled peptide substrates SEQ ID NO: 1 or SEQ ID NO: 2, respectively. The observed fluorescence increases with increasing enzymatic activity, indicating proteolytic cleavage at a peptide bond N-terminal to the phosphoserine residue.

FIG. 14 shows an assay for protein phosphatase activity using either phosphatase PP-2Cα or PP2A. The phosphatases were incubated with rhodamine-labeled phosphorylated Kemptide as the enzyme substrate.

FIG. 15 shows the assay for PKA activity using fluorescein labeled Kemptide substrates.

FIG. 16 shows the assay for PKA activity using Oregon Green labeled Kemptide substrates.

DETAILED DESCRIPTION OF THE INVENTION

The present invention provides an improved method for assaying the catalytic activity of enzymes in a homogenous assay format. As particularly illustrated herein, but without limitation thereto, the method is useful for measuring catalytic activity of (a) kinases in phosphorylating peptide substrates, (b) phosphatases in dephosphorylating peptide substrates, and (c) proteases in cleaving peptide substrates. The method relies on 1) the ability of a paramagnetic metal ion to exhibit specific affinity interaction with a target group on a fluorophore labeled enzyme substrate or endproduct and 2) the ability of the paramagnetic metal ion, when so bound, to quench specifically and preferentially the fluorescent emission of the dye labeled enzyme substrate or endproduct. The concurrent use of these two features together permits the construction of useful enzymatic assays. A requirement of the assay is the inclusion of the fluorophore as a label to enable the quench-based assay of the instant invention, and in most instances a single fluorophore will be the only dye moiety labeled on the substrate.

As used herein, fluorescence quenching (or quenching) refers to a reduction in the observed fluorescent emission intensity from a parent fluorophore relative to its intrinsic or expected fluorescent character. Many of the known characteristics associated with fluorescence quenching and assays that rely on a quenching mechanism, and fluorescence principles in general, are described in Principles of Fluorescence Spectroscopy, 2nd edition, Joseph R. Lakowicz, Kluwer Academic/Plenum Publishers, New York, 1999. A homogenous assay for determining enzymatic activity, based on fluorescent intensity, employing a quenching mechanism requiring only a single dye molecule distinguishes the quench based assay of this invention from other available quench assays, including those based on FRET, and is accompanied by the advantages described herein.

As indicated above, an important aspect of this invention is the use of a paramagnetic metal ion having the ability to complex with a target group on the substrate or endproduct and thereby effect specific quenching of fluorescence of a label thereon. As used herein, a "paramagnetic" ion is an ion having unpaired electrons as indicated in "Advanced Inorganic Chemistry, 4th ed.," p. 1359, by F. A. Cotton and G. Wilkinson.

Metal ions useful in this invention are those that are paramagnetic and have been recognized as having utility in immobilized affinity column chromatography where their specific binding capacity has been used for purification purposes. Particularly useful paramagnetic ions include $Fe^{+++}$ and $Ni^{++}$ (also identified herein as ferric ion or Fe (III), or Ni (II)). $Fe^{+++}$ exhibits specific binding to phosphoryl groups. Thus, in these assays the phosphoryl is the target group for binding to the paramagnetic metal ion to form a complex. Accordingly, $Fe^{+++}$ is especially useful in enzymatic assays involved with phosphorylation or dephosphorylation of substrates. $Ni^{++}$ finds particular utility due to its capacity for specific binding the imidizole target group on histidine and polyhistidine tags. Thus, it is particularly useful in protease assays, where the enzyme substrate incorporates these groups.

To achieve formation of the complex of ion and target, the ion can simply be brought into contact with a fluorescent labeled substrate or endproduct in an aqueous incubation mixture derived from a simple salt such as $FeCl_3$ or $NiCl_2$. It is convenient to contact the paramagnetic metal ion with the substrate or endproduct in a pre-prepared aqueous form coordinated with a chelator. Such chelation improves handling characteristics, solubility, and aqueous stability of the paramagnetic metal ion. Representative chelators for $Fe^{+++}$ and $Ni^{++}$ are iminodiacetic acid (IDA), ethylenediaminetetraacetic acid (EDTA), nitrilotriacetic acid (NTA), or salts thereof, as well as forms where the chelator is attached to a carrier molecule, such as a protein. Salts of paramagnetic metal ions presented to the enzyme substrate or endproduct as simple chelates are preferable by allowing the delivery of higher amounts of the paramagnetic metal ion to the incubation mixture for overcoming the impact of interfering compounds. The utilization of multiple paramagnetic metal ions chelated to a carrier molecule can be employed where it is desired to increase the local molar ratio of the paramagnetic metal ion that can be bound in proximity to the fluorophore when the paramagnetic metal ion binds to its target group.

In practicing this invention, the amount of the paramagnetic metal ion added, in a working solution, to the incubation mixture should be sufficient to provide enough material to bind fully the target groups on the peptide in the mixture. For practical applications, a slight excess is typically used. A slight excess of metal ion improves the functional aspects of the assay with respect to reproducibility and robustness. Where there may be interfering compounds, such as in the case of phosphorylation kinase assays, due to the presence of material in the incubation mixture capable of also binding $Fe^{+++}$, such as ATP and its byproduct, ADP, a larger excess can be used to increase further the reproducibility and robustness of the assay. With the above factors in mind, consideration also should be given to the fact that the paramagnetic metal ion can function as a collisional quencher, and thereby reduce the total fluorescent signal available for detection. Consequently, the optimum concentration of the paramagnetic metal is a concentration providing the maximum differential fluorescent signal and will be dependent on the labeled peptide concentration, along with the instrumentation and format desired to conduct the assays. Table 1 presented hereafter illustrates useful concentrations of the paramagnetic metal ion as presented within the context of a working solution for the typical conditions encountered in plate assays. These concentrations were utilized in examples presented hereafter unless otherwise indicated.

The paramagnetic metal ion can be delivered to the incubation mixture within a buffering solution, which serves to maintain the pH of the final solution (the solution prior to fluorescent measurement). The paramagnetic metal ion also may be delivered to the incubation mixture with additives, such as detergents and solvents.

With respect to pH, a final pH for the solution is selected that avoids potential precipitation of any of the components, while maintaining appropriate pH to allow for specific binding of the paramagnetic metal ion to its target group. In cases where ferric ion is utilized in phosphorylation/dephosphorylation enzyme assays, the utilization of acidic pH values are useful and serve the added function of facilitating stopping the enzymatic reaction in the incubation mixture. The addition of the paramagnetic metal ion can also facilitate stopping of the enzymatic reaction by other mechanisms. For example, in the case of kinase assays, the addition of the ferric ion can facilitate the termination of enzymatic activity by binding to the phosphoryl group of ATP and thereby making the ATP unavailable for enzymatic reaction.

Regarding the ability of the bound paramagnetic metal ion to effect specific quenching, the ion when bound to the target is in proximity to the fluorescent dye label. This spatial requirement can be met by choosing an enzyme substrate or enzyme endproduct where the target group for binding the paramagnetic metal ion is less than about 50 amino acids in length removed from the fluorophore. For practical purposes a spatial separation of less than about 25 amino acids and generally 2 to 10 amino acids is considered useful. However, it should be recognized that the spatial separation of a given labeled peptide in a linear primary structure can differ from the actual spatial separation in solution, for example, due to its secondary and tertiary structure in solution.

In practicing the assay of this invention, customary enzymatic reaction conditions are carried out to allow for the desired conversion of substrate to endproduct. The addition of the paramagnetic metal ion causes the metal ion to bind specifically to a portion of the total initial dye-labeled peptide substrate population. This specific binding event distinguishes enzymatic activity by allowing for discrimination of the enzymatically altered portion of the substrate in relation to that portion of the substrate not altered, or not acted upon, by the enzyme. In practicing the invention, the observed fluorescent emission of the unknown sample can be compared to that of an external reference. The reference can be a control, calibrator, or standard curve, which is optionally predetermined.

The assay of this invention utilizes simple instrumentation. Because the assay is homogenous, no separation steps are required. Additionally, the only instrumentation required to practice this invention is a conventional fluorometer or plate reader. There is no requirement in the assay for measuring changes in polarization signal as is the case in an FP assay and, therefore, no necessity for instrumentation to measure FP. Furthermore, using this assay, many technical limitations associated with other assays are minimized. The instant invention enables a universal approach to assay construction through the use of a single fluorophore, while reducing assay costs and simplifying assay design and data interpretation.

The present invention can be practiced in any of the usual enzymatic reaction formats. Thus, a dye labeled peptide substrate is first prepared, being selected according to desired specificity for the enzyme of choice. The labeled peptide may utilize any of the recognized fluorophores as the dye. Examples of dyes considered to be useful include Lissamine Rhodamine, BODIPY dyes (Molecular Probes, Inc., Eugene, Oreg.), fluorescein, and Oregon Green. Other examples of fluorescent dyes are other dyes supplied by Molecular Probes, as well as those fluorescent dyes manufactured by Amersham and Dyomics and others. Preparation of the dye labeled peptide substrate is accomplished by commonly known procedures. For example, attachment of the fluorophore to the peptide sequence is conveniently accomplished during peptide synthesis by reaction of the N-terminus amino group of the peptide with the dye. A electrophilic, reactive derivative of the fluorophore, such as a sulfonyl chloride derivative, may be utilized to effect the covalent attachment of the fluorophore to the N-terminal alpha amino group of the peptide. However, other methods of attachment and at other locations can be utilized.

Turning specifically to the practice of the present invention with respect to the measurement of kinase activity, a population of dye-labeled peptide substrate is initially phosphorylated in conventional fashion in an incubation mixture (i.e., the enzyme reaction cocktail). The incubation mixture is prepared in a buffer, such as Tris or HEPES. The mixture includes, as essential constituents, the protein kinase of interest (generally serine/threonine kinases or tyrosine kinases), a source of high energy phosphate group such as ATP, and dye-labeled peptide substrate. It may also include other additives, such as enzyme cofactors (e.g., $Ca^{+2}$ and $Mg^{+2}$) for enhancing activity, activators for the enzyme (e.g., phosphatidyl-L-serine for conventional protein kinase C (PKC) isoforms and cyclic AMP for PKA). The mixture can be further supplemented with common enzyme stabilizing agents, such as a reducing agent (i.e., dithiothreitol) or a detergent (i.e., Triton X-100). In many assays, particularly for drug screening, putative inhibitors or enhancers to be evaluated as to their influence on enzyme activity are present.

The mixture, as above prepared, is allowed to incubate for a selected period of time, generally about 10 minutes to 3 hours, to achieve that degree of phosphorylation of the substrate population indicative of the activity of the enzyme in the fashioned environment of the incubation mixture. At this point, the enzyme reaction mixture contains a population of dye-labeled phosphorylated endproduct and non-phosphorylated substrate. Then, in accordance with the present invention, ferric ion ($Fe^{+++}$) is added to the incubation mixture to supply the paramagnetic metal ion. After addition of this ion, the relative fluorescence units (RFU) are measured on a fluorometer. The measured RFU value will be less than that observed for a control sample treated in like fashion but without enzymatic turnover. This decrease is due to the substantially complete quenching by $Fe^{+++}$ of the fluorescent signal from the dye labeled on the phosphorylated peptides in the population, whereas the non-phosphorylated peptide is not quenched to the same degree. A comparison of the decreased fluorescent emission of this mixture with that of the control is a measure of enzyme activity for a given assay; a larger decrease in fluorescent signal indicating more phosphorylation and, in turn, enhanced enzyme activity.

In practicing the invention with respective to determination of protein phosphatase activity, conditions as described above for the kinase enzyme activity can be employed with modifications chosen to reflect the requirements for enzymatic activity of the selected protein phosphatase. ATP, for example, can be omitted. In contrast to the observed assay response of a decrease in observed fluorescence with increasing enzymatic activity, the observed fluorescence will be increased with increased enzymatic activity of the selected protein phosphatase. By definition, the protein phosphatase will require the use of a phosphorylated dye labeled peptide substrate, and consequently the paramagnetic metal ion will bind essentially completely to the starting substrate as opposed to the enzymatic endproduct.

Turning now to the protease assay, the selected peptide sequence contains a proteolytic cleavage site selected according to the protease of choice. The proteolytic cleavage site sequence is specifically chosen to reside within the total amino acid sequence of the starting substrate between the dye and the specific binding site for the paramagnetic metal binding. If the paramagnetic metal selected for the assay is ferric ion, the binding site can, as with kinases and phosphatases be a phosphorylated amino acid. If the paramagnetic metal selected for the assay is divalent nickel ion, the binding site can be histidine or polyhistidine. With respect to the enzymatic reaction cocktail and conditions required for enzymatic activity, the conditions are selected according to the requirements for the chosen protease, and will be typically conducted in a buffered aqueous solution.

A requirement for the assay is that substrate chosen and the dye-labeled on the substrate allow the enzymatic reaction to proceed. A variety of peptide substrates, as well as conditions for their reaction, for kinases, phosphatases, and proteases are known from the literature that allow for the assay of particular enzymes of choice. Consideration should be given to the fact that modification of the peptide sequence with the fluorophore may influence the nature of the enzymatic reaction as compared to that of a non-labeled substrate.

The selection of the peptide sequences to be utilized in the paramagnetic metal ion based assay of the instant invention, are chosen with the following aspects in mind: 1) the peptide should remain soluble in solution after addition of the paramagnetic metal ion, and 2) the "core" structure of the enzyme substrate or endproduct (i.e., that portion not containing the target of the paramagnetic metal ion for specific binding) should not have the propensity for significant non-specific binding of the paramagnetic metal ion.

When a variety of specific substrates are available for investigation of use within the assay, the substrate providing the highest preferential or differential quenching between the enzyme substrate and enzyme endproduct forms will allow for the highest detection sensitivity with respect to enzymatic conversion. The differential response of the enzyme substrate and endproduct forms can be easily determined. For example, in the case of kinase assays, this can be accomplished by first obtaining a sample of the phosphorylated and non-phosphorylated peptides and then diluting them separately to low and essentially equal concentrations to provide for substantially identical fluorescence emission after excitation at a chosen wavelength. Preferably, the concentration of the fluorophore should provide an absorbance at the excitation wavelength sufficiently low to avoid inner filter effects. The $Fe^{+++}$ reagent is added in sequential and identical increments and the fluorescence emission is captured after each addition. The emission intensity of the fluorophore labeled peptides vs. amount of added reagent is then compared; obtaining differential and preferential quenching of the phosphorylated form as compared to the non-phosphorylated form. Examination of the data dye-labeled illustrates the ability to distinguish, and thus provide an assay for, the two forms of the peptide. The peptide pair yielding the highest differential response identifies the peptide pair providing the highest detection sensitivity.

The assay can be practiced in a variety of solution phase formats, such as in cuvettes or microwell plates; the latter being particularly employed where high throughput capability is required. As to microwell plate format densities (i.e., 96 to 1536 well formats), each of these formats have an upper assay volume limit dictated by the well capacity of each plate type. Higher density plates typically have smaller well volume capacities. Thus, an incubation mixture volume chosen for a 96 well plate may exceed the volume capacity that can be accommodated in a higher density format. It is convenient to scale the incubation mixture through these various formats by relating the amount of paramagnetic metal ion delivered to the well to the volume of incubation mixture. Thus, a more concentrated paramagnetic metal ion reagent may be utilized in higher density plate format. Having the foregoing in mind, the amount of paramagnetic metal ion added to the incubation mixture can be based on the volume of the incubation mixture when it is desired to use the assay in multiple plate formats. This is illustrated in Table 1 below.

In other embodiments of the present invention, homogenous aqueous assays also can be accomplished with the labeled enzyme substrate or paramagnetic metal ion affixed to a solid phase, rather than completely soluble in solution. Examples of solid phases include polystyrene plates, membranes, or glass.

In practicing the present invention, the excitation and emission filters used in measuring fluorescence are selected to provide wavelengths that fall within the excitation/emission spectrum of the fluorophore incorporated on the peptide substrate. In the case of Lissamine Rhodamine, a 560/590 filter excitation/emission filter can be utilized; the 560 filter exciting near the peak absorbance of the dye. When the assay is practiced at high peptide concentrations that result in substantial self quenching, it is preferred to utilize off-peak illumination to limit inner filter effects and thereby increase assay detection sensitivity. In all cases, a requirement for choice of excitation/emission filters utilized in the assay is that the selected combinations not present conditions where the photomultiplier tube is saturated in excess of its capacity for measurement. The fluorometer gain setting is preferably set to allow the largest signal distinction between the experimental sample and that of the reference.

While the invention has been described above with respect to assays of the activity of kinase, phosphatase and protease with peptide substrates, the invention is applicable to the assay of other enzymes relying on substrates other than peptides. As to useful enzymes, they are capable of introducing or removing a target group on a fluorecently labeled substrate or endproduct, and where the target group has the ability to bind to a paramagnetic metal ion. Other enzymes include phospholipases that rely on phospholipid substrates, for example. Other substrates can include, in addition to phospholipids, proteins and cyclic nucleotides, among others.

While the assays described herein use a single fluorophore, it is recognized that a plurality of fluorophores may also be incorporated. The plurality may be used to enhance the effective Stokes shift of the fluorophore excitation/emission spectral separation or be used to increase the effective detection sensitivity of the labeled substrate or endproduct.

The following examples illustrate the invention.

EXAMPLE I

Preparation of Working Solution Containing the Paramagnetic Metal Ion as $Fe^{+++}$ 9 volumes of Reagent A (0.555 M MES, 44.4 mM iminodiacetic acid, sodium salt, pH 5.8) and 1 volume of Reagent B (200 mM $FeCl_3$ in water) are mixed to give a final Working Solution containing 20 mM $Fe^{3+}$, 40 mM iminodiacetic acid, disodium salt, 0.5 M MES (morphilinoethane sulfonic acid buffer) with a final pH of approximately 5.5. This reagent can be further diluted with water to yield 0.5× strength working solution or diluted to 0.25× strength working solution with water, for example. The working solution exhibits a time-dependent color change upon mixing. Visually this appears as a darkening of the solution to a reddish brown coloration. The working solution may be utilized immediately in the assay, or may be prepared a day before. Alternatively, the working solution may be briefly warmed to accelerate the color change to a steady state, and then allowed to cool to room temperature prior to use.

Table 1 illustrates use of the working solutions where a common incubation mixture is directly scaled to accommodate a variety of plate density formats. The amount of $Fe^{+++}$ to incubation mixture is held constant across these possible permutations with respect to the volume of incubations. It can be seen from this table that the amount of buffering agent is also held constant with respect to the volume of incubation mixture across these possible permutations. This format allows for the convenience of moving the assay from one plate format to another while ensuring delivery of sufficient $Fe^{+++}$ reagent and equivalent buffering capacity to maintain final pH consistency. The assay is operational under all the illustrated formats. It can be seen from this table that the assay is flexible with respect to its practice. Preferably, the final well volumes are maximized to limit potential inner filter effects that can occur when higher fluorophore-labeled peptide substrates are utilized in the incubation mixture.

TABLE 1

| | 96 Well Plate | 384 Well Plate | 1536 Well Plate |
|---|---|---|---|
| Incubation mixture volume, ul/well/assay | 30 | 18 | 3 |
| Working Solution Addition, ul/well/assay | 120 (0.25 × $Fe^{3+}$ WS) | 36 (0.5 × $Fe^{3+}$ WS) | 3 (1 × $Fe^{3+}$ WS) |
| Final Volume/well | 150 ul | 54 ul | 6 ul |

EXAMPLE II

Fluorescent Measurements

Fluorescent measurements were generally obtained using a BMG PolarStar fluorometric plate reader (BMG Labtechnologies Inc, Durham, N.C.) using a 560/590 filter set, unless otherwise specified. A Tecan Sapphire plate reader (Austria) with a 560/590 excitation/emission and 5 nm bandpass to achieve similar results.

EXAMPLE III

Enzymatic Reaction Conditions for Kinase Enzymes

PKC (protein kinase C) assays were carried out in a reaction mixture consisting of 20 mM HEPES, 5 mM $CaCl_2$, 5 mM $MgCl_2$, 1 mM ATP (disodium salt), 1 mM DTT (dithiothreitol), 0.2 mg/ml phosphatidyl-L-serine, pH 7.4. The enzyme preparation (purified PKC containing alpha, beta, and gamma isoforms, Pierce Biotechnology, Rockford, Ill.) was diluted in 20 mM HEPES, 0.05% Triton X-100, pH 7.4, immediately before use in the assay. The enzyme substrates used were either Myelin Basic Protein Peptide 4-14 SEQ ID NO: 3) or Glycogen Synthase Peptide (SEQ ID NO: 4) or Pseudosubstrate Peptide (SEQ ID NO: 5) labeled on the N-terminal amine with Lissamine Rhodamine.

PKA (protein kinase A) assays were carried out in a reaction mixture consisting of 20 mM HEPES, 0.1 mM cAMP, 5 mM $MgCl_2$, 1 mM ATP (disodium salt), 1 mM DTT, pH 7.4. The enzyme preparation (PKA catalytic unit, Promega, Madison, Wis.) was diluted in 20 mM HEPES, 0.05% Triton X-100, pH 7.4, immediately before use in the assay. The enzyme substrate was Kemptide having a sequence of SEQ ID NO: 6 and labeled on the N-terminal amine Lissamine Rhodamine.

Tyrosine kinase (Src p60c-src, partially purified, Upstate Biotechnology, Waltham, Mass.) assays were carried out in a reaction mixture consisting of 20 mM HEPES, 5 mM $MgCl_2$, 1 mM ATP (disodium salt), 1 mM DTT, pH 7.4. The enzyme substrate Tyrosine Kinase Peptide having a sequence of SEQ ID NO: 7 and labeled on the N-terminal alpha amine with Lissamine Rhodamine.

Enzyme activity for PKC, PKA and tyrosine kinase is stated in mU (milliUnits), where 1 mU of transfers 1 pmole of phosphate per minute under conditions determined by the vendor.

EXAMPLE IV

Detection of Differential Phosphorylation

Enzyme reactions were conducted according to Example III, and following enzymatic reaction, the Working Solution prepared according to Example I was added, thus stopping the reaction. The plates were then measured for fluorescent signal. FIGS. 1-5 illustrate the results.

The following Examples, V and VI, illustrate the assay system of the present invention in assaying differential kinase enzymatic activity in the presence of inhibitors.

EXAMPLE V

Staurosporine PKC Inhibition

Staurosporine, a known ATP-site protein kinase inhibitor, was titrated out in triplicate in 10% DMSO over 22 wells in black 384-well polystyrene Labsystems plates. PKC enzyme and Lissamine Rhodamine labeled Pseudosubstrate peptide were added to a final concentration of 0.04 Units and 60 µM, respectively, in a final reaction concentration of 20 mM HEPES, pH 7.4, 1.0 mM $CaCl_2$, 5 mM $MgCl_2$, 1 mM DTT, and 0.2 mg phosphatidyl-L-serine. 10 µM ATP was added to start the reaction. The final incubation mixture in the well was 18 µl. The reaction was stopped at 90 minutes with the addition of the Working Solution prepared according to Example I and then diluted with 10 volumes of water. Fluorescence was measured using a BMG FluoStar plate reader with a 544/590 ex/em filter set. The results are illustrated in FIG. 6. The calculated $IC_{50}$ was found to be 0.8 nM.

EXAMPLE VI

PKI, PKA Inhibition

PKI, a known synthetic peptide inhibitor of PKA, was titrated out in triplicate in 0.1 mg/ml BSA over 14 wells in black 384-well polystyrene Labsystems plates. PKA enzyme and Lissamine Rhodamine-labeled Kemptide substrate were added to a final concentration of 0.02 Units and 60 µM, respectively, in a final reaction concentration of 20 mM HEPES, pH 7.4, 5 mM $MgCl_2$, and 1 mM DTT. 1.0 mM ATP was added to start the reaction. The reaction was stopped at 90 minutes with the addition of the Working Solution prepared according to Example I and then diluted with 10 volumes of water. Fluorescence was measured using a BMG FluoStar plate reader with a 544/590 ex/em filter set. The results are illustrated in FIG. 7. The calculated $IC_{50}$ was 2.6 nM.

EXAMPLE VII

Enzymatic Reaction Conditions for Phosphatase Enzymes

PTP-Beta and PTP-1 B (commercially available protein tyrosine phosphatases) assays were carried out in a reaction mixture consisting of 20 mM HEPES, 1.5 mM DTT, and 0.5 mM EDTA, pH 7.4. The enzyme substrate used for both enzymes was Lissamine Rhodamine labeled on the N-terminal amine of the following phosphotyrosine peptide substrate (SEQ ID NO: 8).

A PP2A (protein serine/threonine phosphatase) assay was carried out in a reaction mixture consisting of 20 mM HEPES, 1.5 mM DTT, pH 7.4. The enzyme substrate was Lissamine Rhodamine labeled on the N-terminal amine of phospho Kemptide having a sequence of SEQ ID NO: 1.

EXAMPLE VIII

Detection of Differential Dephosphorylation

Enzyme reactions were conducted according to Example VII, and following enzymatic reaction, the Working Solution prepared according to Example I was added. The plates were then measured for fluorescent signal. FIGS. 8 and 9 illustrate the results.

The following Examples, IX and X, illustrate the assay system of the present invention in assaying differential phosphatase enzymatic activity in the presence of inhibitors.

EXAMPLE IX

Sodium Ortho Vanadate, PTP-1B Phosphatase Inhibition

Sodium Ortho Vanadate, a known general phosphatase inhibitor, was titrated in triplicate in 20 mM HEPES, pH 7.4, over 24 wells in a white 96-well polystyrene Coster plate. PTP-1B phosphatase enzyme and Lissamine Rhodamine labeled PhosphoTyrosine peptide substrate in Example VII were added to a final concentration of 22 mUnits and 30 µM, respectively, in a final reaction mixture of 20 mM HEPES. The final incubation mixture in the well was 30 µl. The reaction was stopped at 60 minutes with the addition of the Working Solution prepared according to Example I and then diluted with 30 volumes of water. Fluorescence was measured using a BMG FluoStar plate reader with a 560/590 ex/em filter set. The results are illustrated in FIG. 11. The calculated $IC_{50}$ was found to be 1.0 µM.

EXAMPLE X

Okadaic Acid/PP2A Phosphatase Inhibition

Okadaic Acid, another phosphatase inhibitor, solubilized in DMSO, was titrated in triplicate in phosphatase dilution buffer over 24 wells in white 96-well polystyrene COSTAR plate. PP2A Phosphatase enzyme and Lissamine Rhodamine labeled phospho Kemptide peptide substrate in Example VII were added to a final concentration of 22 milli Units and 30 µM, respectively. The final incubation mixture in the well was 30 µl. The reaction was stopped at 60 minutes with the addition of the Working Solution prepared according to Example I and then diluted with 30 volumes of water. Fluorescence was measured using a BMG FluoStar plate reader with a 560/590 ex/em filter set. The results are illustrated in FIG. 10. The calculated $IC_{50}$ was found to be 1.5 nM.

EXAMPLE XI

Enzymatic Reaction Conditions for Protease Enzymes

The protease, Trypsin (TPCK treated), from Pierce Biotechnology, Inc., which cleaves peptide substrates C-terminal of arginine and lysine residues, was assayed (BAEE units/mg protein) in a reaction mixture consisting of 25 mM TRIS, 150 mM NaCl, pH 7.2. The enzyme substrates used were Lissamine Rhodamine labeled on the N-terminal amine of either phosphoKemptide having a sequence of SEQ. ID. NO. 1 or a longer derivative thereof having the sequence SEQ. ID NO: 2.

EXAMPLE XII

Detection of Differential Cleavage

Enzyme reactions were conducted according to Example XI, and following enzymatic reaction, the Working Solution prepared in accordance with Example I was added. The plates were then measured for fluorescent signal. FIGS. 12 and 13 illustrate the results.

EXAMPLE XIII

Enzymatic Assays Using Fluorescein and Oregon Green Fluorophore Labels

PKA was diluted in 20 mM HEPES, pH 7.4, w/0.05% TX-100 and incubated in a final reaction buffer consisting of 20 mM HEPES, pH 7.4, 0.1 mM cAMP, 1 mM ATP, 5 mM $MgCl_2$, 1 mM DTT with either fluorescein Kemptide (71.25 uM) or Oregon Green Kemptide as the enzymatic substrate at a final concentration of 71.25 or 114.25 µM, respectively, with a final reaction volume of 30 µl, for a reaction time of 1 hour in a 96 well plate format using an opaque white plate. Subsequently, 120 µl of 0.25×Fe(III) working reagent prepared according to Example I was added to the enzymatic reaction mixture and the fluorescence was measured using a 485/538 ex/em filter set. The results are shown in FIGS. 14 and 15.

EXAMPLE XIV

Time-Dependent Enzymatic Protein Phosphatase Activity Assays

IQ™ Assay of the Ser/Thr protein phosphatases PP-2Cα and PP2A. The phosphatases were incubated with Lissamine Rhodamine-labeled phosphorylated Kemptide as the enzyme substrate. At each time point, the enzyme reaction mixture (10 µl) was stopped by, in place of that outlined in Table 1, the addition of 100 µl 0.25× Working Solution in a 96 well white plate and fluorescence was measured, with a 10 µl portion of a no enzyme reaction mixture control treated in the same fashion at each time point. The amount of enzyme utilized was 6.7 mU or 20 mU/10 µl of enzyme reaction mix for PP-2Cα and PP2A, respectively. The fluorescence was then measured with a 560/590 filter set. The observed fluorescence increased with increasing dephosphorylation of the substrate. The results are shown in FIG. 16.

The disclosures of the patents and other references identified herein are incorporated herein in their entirety.

Preferred embodiments of this invention are described herein, including the best mode known to the inventor for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for assaying the activity of a kinase comprising
   a) contacting a fluorophore-labeled substrate with a kinase and ATP to produce a phosphoryl target group on said substrate; and,
   b) contacting the fluorophore labeled phosphorylated substrate with a paramagnetic metal ion to form a complex of the paramagnetic metal ion with the phosphoryl target group, wherein said complex is in sufficient proximity to the fluorophore to cause specific quenching of the fluorescence from the fluorophore;
   c) measuring the intensity of the observed fluorescent emission from the mixture;
   d) wherein a decrease in the fluorescent emission as compared to an external reference is an indicator of kinase activity.

2. A method for assaying the activity of a phosphatase or protease comprising
   a) contacting a fluorephore-labeled substrate containing a target group complexed with a paramagnetic metal ion in sufficient proximity to the fluorophore to cause specific quenching of the fluorescence from the fluorophore, with a phosphatase or a protease so that cleavage by the phosphatase or protease separates said target group from the rest of the fluorophore labeled substrate, wherein the target group is a phosphoryl group in the case of a phosphatase or an imidazole group in the case of a protease,
   b) measuring the intensity of the observed fluorescent emission from the mixture;
   c) wherein an increase in the fluorescent emission as compared to an external reference is an indicator of phosphatase or protease activity.

3. The method of claims 1 or 2 wherein the paramagnetic metal ion is Fe (III) and the target group is a phosphoryl group.

4. The method of claims 1 or 2 wherein the substrate contains a single fluorophore label, which is the only dye entity attached thereto.

5. The method of claims 1 or 2 wherein the paramagnetic metal ion, in addition to being bound to the target group, is coordinated with a chelator.

* * * * *